United States Patent
Tian et al.

(10) Patent No.: US 12,171,538 B1
(45) Date of Patent: Dec. 24, 2024

(54) THREE-DIMENSIONAL (3D) MAGNETIC PARTICLE IMAGING (MPI) METHOD AND SYSTEM WITHOUT ROTATING FIELD-FREE LINE (FFL)

(71) Applicant: Beihang University, Beijing (CN)

(72) Inventors: Jie Tian, Beijing (CN); Yanjun Liu, Beijing (CN); Yu An, Beijing (CN); Guanghui Li, Beijing (CN)

(73) Assignee: Beihang University, Beijing (CN)

( * ) Notice: Subject to any disclaimer, the term of this patent is extended or adjusted under 35 U.S.C. 154(b) by 0 days.

(21) Appl. No.: 18/762,698

(22) Filed: Jul. 3, 2024

(30) Foreign Application Priority Data

Jan. 31, 2024 (CN) .......................... 202410130903.5

(51) Int. Cl.
*A61B 5/0515* (2021.01)
*G01R 33/12* (2006.01)

(52) U.S. Cl.
CPC ........ *A61B 5/0515* (2013.01); *G01R 33/1276* (2013.01)

(58) Field of Classification Search
CPC .......................... A61B 5/0515; G01R 33/1276
See application file for complete search history.

(56) References Cited

U.S. PATENT DOCUMENTS

| | | | |
|---|---|---|---|
| 2017/0067972 A1* | 3/2017 | Diamond | G01R 33/1276 |
| 2018/0206757 A1* | 7/2018 | Goodwill | A61B 5/0515 |
| 2021/0405134 A1 | 12/2021 | Lim et al. | |

FOREIGN PATENT DOCUMENTS

| | | |
|---|---|---|
| CN | 102481111 A | 5/2012 |
| CN | 112684391 A | 4/2021 |
| CN | 114246574 A | 3/2022 |
| CN | 115153490 A | 10/2022 |
| CN | 115886773 A | 4/2023 |
| CN | 116019436 A | 4/2023 |
| WO | 2011116229 A2 | 9/2011 |
| WO | 2016156340 A1 | 10/2016 |

OTHER PUBLICATIONS

Liu Yangyang, et al., Design and Analysis of Magnetic Field-Free Line in Magnetic Particle Imaging, Transactions of China Electrotechnical Society, 2020, pp. 2088-2097, vol. 35 No. 10.

* cited by examiner

*Primary Examiner* — Daniel R Miller
(74) *Attorney, Agent, or Firm* — Bayramoglu Law Offices LLC

(57) ABSTRACT

A three-dimensional (3D) magnetic particle imaging (MPI) method and system without rotating a field-free line (FFL) are disclosed. In accordance with the method, an FFL is generated such that magnetic particles in a region far from the FFL enter a magnetic saturation state. Further, a non-uniform mixed-frequency excitation magnetic field parallel to the FFL is applied to generate intermodulation response signals. In addition, the intermodulation response signals are acquired, amplified and filtered. Moreover, the intermodulation response signals are transmitted to a digital signal processing unit and an image reconstruction unit, and an encoding matrix is constructed. Additionally, a one-dimensional (1D) concentration distribution of the magnetic particles is reconstructed based on the encoding matrix and an actually measured voltage signal. The FFL is driven for line-by-line scanning along a vertical plane of the FFL, thereby achieving 3D imaging.

10 Claims, 2 Drawing Sheets

Generate, by an electromagnetic coil or a permanent magnet, a FFL at a center of an imaging field of view, such that magnetic particles in a region far from the FFL enter a magnetic saturation state

↓

Apply a non-uniform mixed-frequency excitation magnetic field parallel to the FFL, so as to excite magnetic particles at different positions on the FFL to generate unique intermodulation response signals

↓

Acquire, by a receiving coil parallel to the FFL, the intermodulation response signals on the FFL

↓

Construct an encoding matrix based on the intermodulation response signals at different positions on the FFL

↓

Reconstruct a 1D concentration distribution of the magnetic particles on the FFL based on the encoding matrix and an actually measured voltage signal

↓

Drive the FFL for line-by-line scanning along a vertical plane of the FFL by applying an orthogonal magnetic field perpendicular to the FFL, thereby achieving 3D imaging

FIG. 1 ing time and manufacturing cost of FFL-type MPI systems without sacrificing spatial resolution.

In view of this, the present disclosure provides a three-dimensional (3D) MPI method and system without rotating an FFL.

THREE-DIMENSIONAL (3D) MAGNETIC PARTICLE IMAGING (MPI) METHOD AND SYSTEM WITHOUT ROTATING FIELD-FREE LINE (FFL)

CROSS-REFERENCE TO THE RELATED APPLICATIONS

This application is based upon and claims priority to Chinese Patent Application No. 202410130903.5, filed on Jan. 31, 2024, the entire contents of which are incorporated herein by reference.

TECHNICAL FIELD

The present disclosure relates to the field of biomedical imaging, and specifically to a three-dimensional (3D) magnetic particle imaging (MPI) method and system without rotating a field-free line (FFL).

BACKGROUND

Magnetic nanoparticles, which are superparamagnetic nanoparticles, have been widely studied and applied as a new type of medical imaging tracer in biomedical practices such as tumor detection, magnetic particle hyperthermia (MPH), and targeted drug delivery.

Magnetic particle imaging (MPI) is a novel biomedical imaging technique that generates a stable magnetic field-free region (FFR) at the center of the field of view by applying a static gradient magnetic field. According to the magnetic saturation effect, magnetic nanoparticles at and near the FFR can generate dynamic magnetization response due to the excitation of an alternating magnetic field. In contrast, magnetic nanoparticles far from the FFR are saturated with a strong magnetic field and hard to generate dynamic magnetization response. Therefore, by superposing bias magnetic fields in different directions on the basis of the static gradient magnetic field and the excitation magnetic field, the FFR can be moved for spatial scanning, thereby achieving spatial encoding. The spatial distribution of magnetic nanoparticles can be localized and imaged through the dynamic magnetization response signals at different positions of the FFR.

According to the different topological structures of gradient coils, there are two types of FFRs: field-free point (FFP) and field-free line (FFL). FFP-type MPI can acquire magnetic nanoparticle signals within a pixel area at once, thereby achieving high spatial resolution. However, due to the fact that the signals acquired at once come from only one pixel area, FFP-type MPI has low sensitivity and signal-to-noise ratio (SNR). Comparatively speaking, FFL-type MPI can simultaneously acquire magnetic nanoparticle signals on a single line, thereby achieving higher sensitivity and SNR. However, to acquire the position information of magnetic nanoparticles on the FFL, traditional methods require multi-angle rotation of the FFL for signal acquisition and spatial encoding, which greatly increases the overall imaging time. In addition, the rotation of the FFL requires complex mechanical design, and also requires high power consumption if magnetic field rotation is adopted. Therefore, despite the high sensitivity and SNR, the current FFL-type MPI technique requires high time and economic costs to acquire high-resolution images.

In order to achieve high-sensitivity and high-resolution MPI, there is a need for a method that can reduce the

SUMMARY

In order to solve the above-mentioned problems in the prior art, that is, long overall imaging time and the need for complex mechanical design and high power consumption to rotate a field-free line (FFL), the present disclosure provides a three-dimensional (3D) MPI method and system without rotating an FFL.

A first aspect of the present disclosure provides a three-dimensional (3D) magnetic particle imaging (MPI) method without rotating a field-free line (FFL), including:

generating, by an FFL generation module, an FFL at a center of an imaging field of view, such that magnetic particles in a region far from the FFL enter a magnetic saturation state;

applying a non-uniform mixed-frequency excitation magnetic field parallel to the FFL, so as to excite magnetic particles at different positions on the FFL to generate intermodulation response signals;

acquiring, by a receiving coil parallel to the FFL, the intermodulation response signals on the FFL; and amplifying and filtering the intermodulation response signals, and transmitting the intermodulation response signals to a digital signal processing unit and an image reconstruction unit;

constructing an encoding matrix based on multiple intermodulation response signals processed by the digital signal processing unit;

reconstructing, by the image reconstruction unit, a one-dimensional (1D) concentration distribution of the magnetic particles on the FFL based on the encoding matrix and an actually measured voltage signal; and driving the FFL for line-by-line scanning along a vertical plane of the FFL by applying an orthogonal magnetic field perpendicular to the FFL, thereby achieving 3D imaging.

In some preferred implementations, the magnetic saturation state refers to a state where the magnetic particles no longer generate dynamic magnetization response signals to the alternating magnetic field.

In some preferred implementations, the non-uniform mixed-frequency excitation magnetic field includes alternating magnetic fields of at least two frequencies: a high-frequency uniform magnetic field and a low-frequency gradient magnetic field; the high-frequency uniform magnetic field is configured to simultaneously excite the magnetic particles on the FFL to generate magnetization response signals with a high signal-to-noise ratio (SNR); and the low-frequency gradient magnetic field is configured to spatially encode the magnetic particles on the FFL, such that the magnetic particles at different positions on the FFL generate different magnetization response signals.

In some preferred implementations, the intermodulation response signals refer to different magnetization response signals of the magnetic particles at different positions on the FFL, and the magnetization response signals are mixed-frequency signals; and the intermodulation response signals each include two excitation frequency components and a frequency component after intermodulation of two excitation frequencies; and the intermodulation response signals are time-domain or frequency-domain signals.

In some preferred implementations, the encoding matrix is constructed by:

placing magnetic particle samples with a preset voxel size at different positions on the FFL, acquiring intermodulation response signals at different positions, forming an encoding vector with the intermodulation response signals at each position, and forming the encoding matrix by encoding vectors corresponding to the intermodulation response signals at different positions.

Another aspect of the present disclosure provides a 3D MPI system without rotating an FFL, based on the 3D MPI method without rotating an FFL, and including the FFL generation module, a non-uniform mixed-frequency excitation module, an FFL signal acquisition module, an FFL translation module, the digital signal processing unit, and the image reconstruction unit, where the FFL generation module includes a first constant gradient magnetic field generator and a second constant gradient magnetic field generator with an axial direction along a Y-axis, and is configured to generate the FFL within the imaging field of view;

the non-uniform mixed-frequency excitation module includes a first high-frequency uniform magnetic field generator and a second high-frequency uniform magnetic field generator with an axial direction along an X-axis, as well as a first low-frequency gradient magnetic field generator and a second low-frequency gradient magnetic field generator;

the first high-frequency uniform magnetic field generator and the second high-frequency uniform magnetic field generator are configured to simultaneously excite the magnetic particles on the FFL to generate the magnetization response signals with a high SNR; and the first low-frequency gradient magnetic field generator and the second low-frequency gradient magnetic field generator are configured to cause the magnetic particles at different positions on the FFL to generate different magnetization response signals;

the FFL signal acquisition module includes a first receiving coil and a second receiving coil with an axial direction along the X-axis, and is configured to acquire the dynamic magnetization response signals of the magnetic particles on the FFL; the FFL signal acquisition module further includes a signal amplification and filtering circuit connected to the first receiving coil and the second receiving coil; and the signal amplification and filtering circuit is configured to amplify and filter the dynamic magnetization response signals;

the FFL translation module includes a first scanning magnetic field generator and a second scanning magnetic field generator with an axial direction along the Y-axis, and is configured to drive the FFL to move and scan along the Y-axis;

the digital signal processing unit is connected to the signal amplification and filtering circuit, and is configured to perform Fourier transform and frequency selection on time-domain signals in the dynamic magnetization response signals of the magnetic particles on the FFL;

the image reconstruction unit is connected to the digital signal processing unit, and is configured to perform image reconstruction in combination with a voltage signal corresponding to a selected frequency component and the encoding matrix; and the Y-axis and the X-axis are respectively determined based on an axis direction of the FFL generation module and a length direction of the FFL.

In some preferred implementations, the first constant gradient magnetic field generator and the second constant gradient magnetic field generator are symmetric with the FFL in an initial state as an axis of symmetry.

In some preferred implementations, the first scanning magnetic field generator and the second scanning magnetic field generator are coaxial with the first constant gradient magnetic field generator and the second constant gradient magnetic field generator, and are located between the first constant gradient magnetic field generator and the second constant gradient magnetic field generator; and the first scanning magnetic field generator and the second scanning magnetic field generator are symmetric with the FFL in the initial state as an axis of symmetry.

In some preferred implementations, the first high-frequency uniform magnetic field generator and the second high-frequency uniform magnetic field generator are located between the first scanning magnetic field generator and the second scanning magnetic field generator;

the first high-frequency uniform magnetic field generator and the second high-frequency uniform magnetic field generator are symmetric with the FFL in the initial state as an axis of symmetry;

the first low-frequency gradient magnetic field generator and the second low-frequency gradient magnetic field generator are located between the first high-frequency uniform magnetic field generator and the second high-frequency uniform magnetic field generator; and the first low-frequency gradient magnetic field generator and the second low-frequency gradient magnetic field generator are symmetric about a symmetry point; and the symmetry point is a midpoint of a vertical line connecting centers of the first constant gradient magnetic field generator and the second constant gradient magnetic field generator.

In some preferred implementations, the first receiving coil and the second receiving coil are located between the first high-frequency uniform magnetic field generator and the second high-frequency uniform magnetic field generator, and are coaxial with the first high-frequency uniform magnetic field generator and the second high-frequency uniform magnetic field generator;

the first receiving coil and the second receiving coil are symmetric with the FFL in the initial state as an axis of symmetry; and the FFL is located between the first receiving coil and the second receiving coil.

The present disclosure has following beneficial effects:

In the present disclosure, a non-uniform mixed-frequency excitation magnetic field is applied along the FFL to excite magnetic particles at different positions on the FFL to generate unique intermodulation response signals. The intermodulation response signals of the magnetic particles at different positions are acquired to construct an encoding matrix, and a one-dimensional (1D) distribution of a magnetic particle concentration on the FFL is reconstructed. An orthogonal scanning coil is used to achieve two-dimensional (2D) translation scanning of the FFL, thereby achieving 2D and 3D imaging. The present disclosure creatively proposes the excitation method for the non-uniform mixed-frequency excitation of the FFL, which can quickly acquire the position information of the magnetic particles on the FFL without the need to rotate the FFL. The present disclosure avoids complex mechanical rotation and high power consumption, and reduces the manufacturing cost and imaging time of the FFL-based MPI system.

BRIEF DESCRIPTION OF THE DRAWINGS

Other features, objectives and advantages of the present disclosure will become more apparent upon reading the detailed description of the non-restrictive embodiments with reference to the following drawings.

FIG. 1 is a flowchart of a three-dimensional (3D) magnetic particle imaging (MPI) method without rotating a field-free line (FFL) according to the present disclosure.

DETAILED DESCRIPTION OF THE EMBODIMENTS

Figure 2:
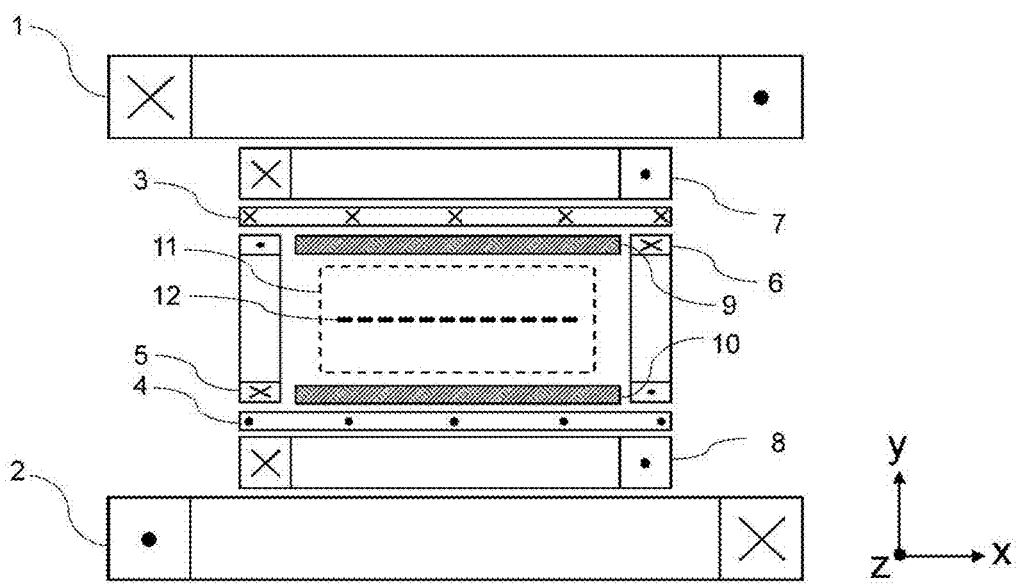
FIG. 2 is a structural diagram of a 3D MPI system without rotating an FFL according to the present disclosure.

The present disclosure will be further described in detail below with reference to the drawings and embodiments. It should be understood that the specific embodiments described herein are merely intended to explain the present disclosure, rather than to limit the present disclosure. It should also be noted that, for convenience of description, only the parts related to the present disclosure are shown in the drawings.

It should be noted that the embodiments in the present disclosure and features in the embodiments may be combined with each other in a non-conflicting situation. The present disclosure will be described in detail below with reference to the drawings and embodiments.

Referring to FIG. 1, the first embodiment of the present disclosure provides a three-dimensional (3D) magnetic particle imaging (MPI) method without rotating a field-free line (FFL), including the following steps.

An FFL is generated by an FFL generation module at a center of an imaging field of view, such that magnetic particles in a region far from the FFL enter a magnetic saturation state.

A non-uniform mixed-frequency excitation magnetic field parallel to the FFL is applied, so as to excite magnetic particles at different positions on the FFL to generate intermodulation response signals.

The intermodulation response signals on the FFL are acquired by a receiving coil parallel to the FFL, amplified and filtered, and transmitted to a digital signal processing unit and an image reconstruction unit.

An encoding matrix is constructed based on multiple intermodulation response signals processed by the digital signal processing unit.

A one-dimensional (1D) concentration distribution of the magnetic particles on the FFL is reconstructed by the image reconstruction unit based on the encoding matrix and an actually measured voltage signal.

The FFL is driven for line-by-line scanning along a vertical plane of the FFL by applying an orthogonal magnetic field perpendicular to the FFL, thereby achieving 3D imaging.

In order to provide a clearer explanation of the 3D MPI method without rotating an FFL in the present disclosure, each step in an embodiment of the present disclosure is described in detail below according to FIG. 1.

An FFL is generated by an FFL generation module at a center of an imaging field of view, such that magnetic particles in a region far from the FFL enter a magnetic saturation state.

In the present disclosure, the magnetic saturation state refers to a state where the magnetization intensity of magnetic nanoparticles no longer freely changes with the change of the magnetic field under the action of a certain strong magnetic field, that is, no long to generate dynamic magnetization response signals to the alternating magnetic field.

A non-uniform mixed-frequency excitation magnetic field parallel to the FFL is applied, so as to excite magnetic particles at different positions on the FFL to generate intermodulation response signals.

In the present disclosure, the intermodulation response signals are unique intermodulation response signals, meaning that the magnetization response signals of magnetic nanoparticles at different positions on the FFL are different. Due to the fact that the excitation magnetic field is mixed, the magnetization response signals are also mixed, including two excitation frequency components and a frequency component after intermodulation of two excitation frequencies.

In the present disclosure, the non-uniform mixed-frequency excitation magnetic field includes alternating magnetic fields of at least two frequencies, namely a high-frequency uniform magnetic field and a low-frequency gradient magnetic field. The high-frequency uniform magnetic field is configured to simultaneously excite the magnetic particles on the FFL to generate magnetization response signals with a high signal-to-noise ratio (SNR). The low-frequency gradient magnetic field is configured to spatially encode the magnetic particles on the FFL, such that the magnetic particles at different positions on the FFL generate different magnetization response signals.

The intermodulation response signals refer to different magnetization response signals of the magnetic particles at different positions on the FFL, and the magnetization response signals are mixed-frequency signals.

The intermodulation response signals each include two excitation frequency components and a frequency component after intermodulation of two excitation frequencies.

The intermodulation response signals on the FFL are acquired by a receiving coil parallel to the FFL, amplified and filtered, and transmitted to a digital signal processing unit and an image reconstruction unit.

An encoding matrix is constructed based on multiple intermodulation response signals processed by the digital signal processing unit.

The encoding matrix includes the intermodulation response signals of the magnetic particles at different positions on the FFL; and the intermodulation response signals are time-domain or frequency-domain signals.

A one-dimensional (1D) concentration distribution of the magnetic particles on the FFL is reconstructed by the image reconstruction unit based on the encoding matrix and an actually measured voltage signal.

Specifically, the encoding matrix is constructed as follows.

Magnetic particle samples with a preset voxel size are placed at different positions on the FFL, intermodulation response signals at different positions are acquired, an encoding vector is formed with the intermodulation response signals at each position, and the encoding matrix is formed by encoding vectors corresponding to the intermodulation response signals at different positions.

The FFL is driven for line-by-line scanning along a vertical plane of the FFL by applying an orthogonal magnetic field perpendicular to the FFL, thereby achieving 3D imaging.

3D imaging is achieved based on multiple 1D concentration distributions of the magnetic particles on the FFL after line-by-line scanning.

These steps are described in order in the above embodiments. However, those skilled in the art may understand that, in order to achieve the effects of these embodiments, different steps may not be necessarily executed in such an order, but may be executed simultaneously (in parallel) or in a reversed order. These simple changes should fall within the protection scope of the present disclosure.

Referring to FIG. 2, a second embodiment of the present disclosure provides a 3D MPI system without rotating an FFL, based on the 3D MPI method without rotating an FFL. The system includes an FFL generation module, a non-uniform mixed-frequency excitation module, an FFL signal acquisition module, an FFL translation module, the digital signal processing unit, and the image reconstruction unit.

The FFL generation module includes first constant gradient magnetic field generator 1 and second constant gradient magnetic field generator 2 with an axial direction along a Y-axis, and is configured to generate FFL 12 within the imaging field of view.

The non-uniform mixed-frequency excitation module includes first high-frequency uniform magnetic field generator 3 and second high-frequency uniform magnetic field generator 4 with an axial direction along an X-axis, as well as first low-frequency gradient magnetic field generator 5 and second low-frequency gradient magnetic field generator 6.

The first high-frequency uniform magnetic field generator 3 and the second high-frequency uniform magnetic field generator 4 are configured to simultaneously excite the magnetic particles on the FFL 12 to generate magnetization response signals with a high SNR. The first low-frequency gradient magnetic field generator 5 and the second low-frequency gradient magnetic field generator 6 are configured to make magnetization response signals of magnetic particles at different positions on the FFL 12 different.

The FFL signal acquisition module includes first receiving coil 9 and second receiving coil 10 with an axial direction along the X-axis, and is configured to acquire the dynamic magnetization response signals of the magnetic particles on the FFL 12. The FFL signal acquisition module further includes a signal amplification and filtering circuit connected to the first receiving coil 9 and the second receiving coil 10. The signal amplification and filtering circuit is configured to amplify and filter the dynamic magnetization response signals.

The FFL translation module includes first scanning magnetic field generator 7 and second scanning magnetic field generator 8 with an axial direction along the Y-axis, and is configured to drive the FFL 12 to move and scan along the Y-axis.

The digital signal processing unit is connected to the signal amplification and filtering circuit, and is configured to perform Fourier transform and frequency selection on time-domain signals in the dynamic magnetization response signals of the magnetic particles on the FFL 12.

The image reconstruction unit is connected to the digital signal processing unit, and is configured to perform image reconstruction in combination with a voltage signal corresponding to a selected frequency component and the encoding matrix.

The Y-axis and the X-axis are respectively determined based on an axis direction of the FFL generation module and a length direction of the FFL 12.

As a further explanation of the present disclosure, the first constant gradient magnetic field generator 1 and the second constant gradient magnetic field generator 2 are symmetric with the FFL 12 in an initial state as an axis of symmetry.

The first constant gradient magnetic field generator 1 and the second constant gradient magnetic field generator 2 are two coils with a same diameter and opposite winding directions.

As a further explanation of the present disclosure, the first scanning magnetic field generator 7 and the second scanning magnetic field generator 8 are coaxial with the first constant gradient magnetic field generator 1 and the second constant gradient magnetic field generator 2, and are located between the first constant gradient magnetic field generator 1 and the second constant gradient magnetic field generator 2.

The first scanning magnetic field generator 7 and the second scanning magnetic field generator 8 are symmetric with the FFL 12 in the initial state as an axis of symmetry.

The first scanning magnetic field generator 7 and the second scanning magnetic field generator 8 are two coils with a same diameter and winding direction.

As a further explanation of the present disclosure, the first high-frequency uniform magnetic field generator 3 and the second high-frequency uniform magnetic field generator 4 are located between the first scanning magnetic field generator 7 and the second scanning magnetic field generator 8.

The first high-frequency uniform magnetic field generator 3 and the second high-frequency uniform magnetic field generator 4 are symmetric with the FFL 12 in the initial state as an axis of symmetry.

The first low-frequency gradient magnetic field generator 5 and the second low-frequency gradient magnetic field generator 6 are located between the first high-frequency uniform magnetic field generator 3 and the second high-frequency uniform magnetic field generator 4.

The first low-frequency gradient magnetic field generator 5 and the second low-frequency gradient magnetic field generator 6 are symmetric about a symmetry point. The symmetry point is a midpoint of a vertical line connecting centers of the first constant gradient magnetic field generator 1 and the second constant gradient magnetic field generator 2.

The present disclosure does not limit the axial direction of the first low-frequency gradient magnetic field generator 5 and the second low-frequency gradient magnetic field generator 6, which can be the X-axis or the Y-axis. As shown in FIG. 2, in this embodiment, the first low-frequency gradient magnetic field generator 5 and the second low-frequency gradient magnetic field generator 6 adopt the X-axial direction as the axial direction and are symmetrically arranged left and right along the symmetry point.

The first high-frequency uniform magnetic field generator 3 and the second high-frequency uniform magnetic field generator 4 are wound in opposite directions and form an integrated solenoid coil. A current flows in from the first high-frequency uniform magnetic field generator 3 and out from the second high-frequency uniform magnetic field generator 4.

In this embodiment, the first low-frequency gradient magnetic field generator 5 and the second low-frequency gradient magnetic field generator 6 are two coils with a same diameter and opposite winding directions.

As a further explanation of the present disclosure, the first receiving coil 9 and the second receiving coil 10 are located between the first high-frequency uniform magnetic field generator 3 and the second high-frequency uniform magnetic field generator 4, and are coaxial with the first high-frequency uniform magnetic field generator 3 and the second high-frequency uniform magnetic field generator 4.

The first receiving coil 9 and the second receiving coil 10 are symmetric with the FFL 12 in the initial state as an axis of symmetry.

The FFL 12 is located between the first receiving coil 9 and the second receiving coil 10.

The first receiving coil 9 and the second receiving coil 10 have a same diameter. The axial direction of the first receiving coil 9 and the second receiving coil 10 is parallel to the length direction of the FFL 12.

The first receiving coil 9 and the second receiving coil 10 form another integrated solenoid coil. A current flows in from the first receiving coil 9 and out from the second receiving coil 10.

The FFL 12 is located within the imaging field of view 11.

Those skilled in the art should clearly understand that, for convenience and brevity of description, reference is made to corresponding processes in the above method embodiments for specific working processes and related description of the system, and details are not described herein again.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described in the preferred implementations with reference to the drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions derived by making these changes or substitutions should fall within the protection scope of the present disclosure.

What is claimed is:

1. A three-dimensional (3D) magnetic particle imaging (MPI) method without rotating a field-free line (FFL), comprising:
   generating, by an FFL generation module, an FFL at a center of an imaging field of view, wherein magnetic particles in a region far from the FFL enter a magnetic saturation state;
   applying a non-uniform mixed-frequency excitation magnetic field parallel to the FFL, to excite magnetic particles at different positions on the FFL to generate intermodulation response signals;
   wherein the non-uniform mixed-frequency excitation magnetic field comprises alternating magnetic fields of at least two frequencies: a high-frequency uniform magnetic field and a low-frequency gradient magnetic field; the high-frequency uniform magnetic field is configured to simultaneously excite the magnetic particles on the FFL to generate magnetization response signals with a high signal-to-noise ratio (SNR); and the low-frequency gradient magnetic field is configured to spatially encode the magnetic particles on the FFL, wherein the magnetic particles at different positions on the FFL generate different magnetization response signals;
   the intermodulation response signals refer to different magnetization response signals of the magnetic particles at different positions on the FFL, and the magnetization response signals are mixed-frequency signals; and
   the intermodulation response signals each comprise two excitation frequency components and a frequency component after intermodulation of two excitation frequencies; and the intermodulation response signals are time-domain or frequency-domain signals;
   acquiring, by a receiving coil parallel to the FFL, the intermodulation response signals on the FFL; and amplifying and filtering the intermodulation response signals, and transmitting the intermodulation response signals to a digital signal processing unit and an image reconstruction unit;
   constructing an encoding matrix, by the digital signal processing unit, based on the intermodulation response signals processed by the digital signal processing unit;
   reconstructing, by the image reconstruction unit, a one-dimensional (1D) concentration distribution of the magnetic particles on the FFL based on the encoding matrix and an actually measured voltage signal; and
   driving the FFL for line-by-line scanning along a vertical plane of the FFL by applying an orthogonal magnetic field perpendicular to the FFL, achieving 3D imaging, wherein the actually measured voltage signal is measured by the imaging coil corresponding to the intermodulation response signals.

2. The 3D MPI method without rotating the FFL according to claim 1, wherein the magnetic saturation state refers to a state where the magnetic particles no longer generate dynamic magnetization response signals to the alternating magnetic field.

3. The 3D MPI method without rotating the FFL according to claim 1, wherein the encoding matrix is constructed by:
   placing magnetic particle samples with a preset voxel size at different positions on the FFL, acquiring the intermodulation response signals at different positions, forming an encoding vector with the intermodulation response signals at each position, and forming the encoding matrix by encoding vectors corresponding to the intermodulation response signals at different positions.

4. A 3D MPI system without rotating an FFL, performing the 3D MPI method without rotating the FFL according to claim 1, and comprising the FFL generation module, a non-uniform mixed-frequency excitation module, an FFL signal acquisition module, an FFL translation module, the digital signal processing unit, and the image reconstruction unit, wherein
   the FFL generation module comprises a first constant gradient magnetic field generator and a second constant gradient magnetic field generator with an axial direction along a Y-axis, and is configured to generate the FFL within the imaging field of view;
   the non-uniform mixed-frequency excitation module comprises a first high-frequency uniform magnetic field generator and a second high-frequency uniform magnetic field generator with an axial direction along an X-axis, as well as a first low-frequency gradient magnetic field generator and a second low-frequency gradient magnetic field generator;
   the first high-frequency uniform magnetic field generator and the second high-frequency uniform magnetic field generator are configured to simultaneously excite the magnetic particles on the FFL to generate the magnetization response signals with the high SNR; and the first low-frequency gradient magnetic field generator and the second low-frequency gradient magnetic field generator are configured to cause the magnetic particles at different positions on the FFL to generate the different magnetization response signals;

the FFL signal acquisition module comprises a first receiving coil and a second receiving coil with an axial direction along the X-axis, and is configured to acquire dynamic magnetization response signals of the magnetic particles on the FFL; the FFL signal acquisition module further comprises a signal amplification and filtering circuit connected to the first receiving coil and the second receiving coil; and the signal amplification and filtering circuit is configured to amplify and filter the dynamic magnetization response signals;

the FFL translation module comprises a first scanning magnetic field generator and a second scanning magnetic field generator with an axial direction along the Y-axis, and is configured to drive the FFL to move and scan along the Y-axis;

the digital signal processing unit is connected to the signal amplification and filtering circuit, and is configured to perform Fourier transform and frequency selection on time-domain signals in the dynamic magnetization response signals of the magnetic particles on the FFL;

the image reconstruction unit is connected to the digital signal processing unit, and is configured to perform image reconstruction in combination with a voltage signal corresponding to a selected frequency component and the encoding matrix; and the Y-axis and the X-axis are respectively determined based on an axis direction of the FFL generation module and a length direction of the FFL.

5. The 3D MPI system without rotating the FFL according to claim 4, wherein the first constant gradient magnetic field generator and the second constant gradient magnetic field generator are symmetric with the FFL in an initial state as an axis of symmetry.

6. The 3D MPI system without rotating the FFL according to claim 5, wherein the first scanning magnetic field generator and the second scanning magnetic field generator are coaxial with the first constant gradient magnetic field generator and the second constant gradient magnetic field generator, and are located between the first constant gradient magnetic field generator and the second constant gradient magnetic field generator; and the first scanning magnetic field generator and the second scanning magnetic field generator are symmetric with the FFL in the initial state as an axis of symmetry.

7. The 3D MPI system without rotating the FFL according to claim 4, wherein the first high-frequency uniform magnetic field generator and the second high-frequency uniform magnetic field generator are located between the first scanning magnetic field generator and the second scanning magnetic field generator;

the first high-frequency uniform magnetic field generator and the second high-frequency uniform magnetic field generator are symmetric with the FFL in an initial state as an axis of symmetry;

the first low-frequency gradient magnetic field generator and the second low-frequency gradient magnetic field generator are located between the first high-frequency uniform magnetic field generator and the second high-frequency uniform magnetic field generator; and the first low-frequency gradient magnetic field generator and the second low-frequency gradient magnetic field generator are symmetric about a symmetry point; and the symmetry point is a midpoint of a vertical line connecting centers of the first constant gradient magnetic field generator and the second constant gradient magnetic field generator.

8. The 3D MPI system without rotating the FFL according to claim 4, wherein the first receiving coil and the second receiving coil are located between the first high-frequency uniform magnetic field generator and the second high-frequency uniform magnetic field generator, and are coaxial with the first high-frequency uniform magnetic field generator and the second high-frequency uniform magnetic field generator;

the first receiving coil and the second receiving coil are symmetric with the FFL in an initial state as an axis of symmetry; and the FFL is located between the first receiving coil and the second receiving coil.

9. The 3D MPI system without rotating the FFL according to claim 4, wherein in the 3D MPI method, the magnetic saturation state refers to a state where the magnetic particles no longer generate the dynamic magnetization response signals to the alternating magnetic field.

10. The 3D MPI system without rotating the FFL according to claim 4, wherein the digital signal processing unit is configured to construct the encoding matrix by:

placing magnetic particle samples with a preset voxel size at different positions on the FFL, acquiring the intermodulation response signals at different positions, forming an encoding vector with the intermodulation response signals at each position, and forming the encoding matrix by encoding vectors corresponding to the intermodulation response signals at different positions.

* * * * *